US012751959B2

(12) United States Patent
Peyravian et al.

(10) Patent No.: US 12,751,959 B2
(45) Date of Patent: Oct. 6, 2026

(54) CANNABIDIOL NANODRUG FORMULATIONS AND METHODS FOR USE OF THE SAME

(71) Applicant: UNIVERSITY OF MIAMI, Miami, FL (US)

(72) Inventors: Nadia Peyravian, Miami, FL (US); Sylvia Daunert, Miami, FL (US); Joaquin J. Jimenez, Miami, FL (US); Suzana Hamdan, Miami, FL (US); Naiem Issa, Miami, FL (US); Sapna K. Deo, Miami, FL (US); Assuan Lens, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 875 days.

(21) Appl. No.: 17/909,194

(22) PCT Filed: Mar. 5, 2021

(86) PCT No.: PCT/US2021/021182
§ 371 (c)(1),
(2) Date: May 15, 2023

(87) PCT Pub. No.: WO2021/178871
PCT Pub. Date: Sep. 10, 2021

(65) Prior Publication Data

US 2023/0143752 A1 May 11, 2023

Related U.S. Application Data

(60) Provisional application No. 63/055,038, filed on Jul. 22, 2020, provisional application No. 62/985,529, filed on Mar. 5, 2020.

(51) Int. Cl.

| | |
|---|---|
| ***A61K 31/00*** | (2006.01) |
| ***A61K 9/00*** | (2006.01) |
| ***A61K 9/14*** | (2006.01) |
| ***A61K 9/16*** | (2006.01) |
| ***A61K 31/506*** | (2006.01) |
| ***A61P 17/14*** | (2006.01) |
| ***A61P 37/06*** | (2006.01) |

(52) U.S. Cl.
CPC .......... *A61K 31/658* (2023.05); *A61K 9/0014* (2013.01); *A61K 9/14* (2013.01); *A61K 9/1688* (2013.01); *A61K 31/506* (2013.01); *A61P 17/14* (2018.01); *A61P 37/06* (2018.01)

(58) Field of Classification Search
CPC ...... A61K 9/14; A61K 9/0014; A61K 31/658; A61K 9/1688
See application file for complete search history.

(56) References Cited

U.S. PATENT DOCUMENTS

| | | | | |
|---|---|---|---|---|
| 7,442,369 | B1 * | 10/2008 | Pena | A61K 8/737 424/78.02 |
| 9,375,417 | B2 | 6/2016 | Smith et al. | |
| 2014/0302121 | A1 * | 10/2014 | Bevier | A61K 9/127 424/491 |
| 2017/0000744 | A1 | 1/2017 | Kaufman | |
| 2017/0100319 | A1 | 4/2017 | Sekhavat | |
| 2018/0296493 | A1 * | 10/2018 | Kaufman | A61K 9/127 |
| 2019/0297882 | A1 | 10/2019 | Aeschbach | |

FOREIGN PATENT DOCUMENTS

| | | | | |
|---|---|---|---|---|
| WO | WO-2013/108254 | A1 | 7/2013 | |
| WO | WO-2014/032152 | A1 | 3/2014 | |
| WO | WO-2017055846 | A1 * | 4/2017 | A61P 17/06 |
| WO | WO-2019/010535 | A1 | 1/2019 | |
| WO | WO-2019/140321 | A1 | 7/2019 | |
| WO | WO-2020186212 | A1 * | 9/2020 | A61K 47/12 |

OTHER PUBLICATIONS

Arias et al (Frontiers in Pharmacology, Sep. 2024, vol. 15, pp. 1-15) (Year: 2024).*
Miller (Current Opinion in Immunology, 2023, vol. 80, pp. 1-9) (Year: 2023).*
Lintzeri (Journal of Deutschen Dermatologischen Gesellschaft, CME article, 2022, pp. 59-90) (Year: 2022).*
Supplementary European Search Report for Application No. 21765120.7, dated Feb. 16, 2024.
Anzai et al., Pathomechanisms of immune-mediated alopecia, Int. Immunol., 31(7):439-47 (2019).
Barry, Novel mechanisms and devices to enable successful transdermal drug delivery, Eur. J. Pharm. Sci., 14(2):101-14 (2001).
Bartner et al., Pharmacokinetics of cannabidiol administered by 3 delivery methods at 2 different dosages to healthy dogs, Can. J. Vet. Res., 82(3):178-83 (2018).
Blanco et al., Nannocannabinoids for brain tumor drug delivery, Anales de la Real Academia Nacional de Farmacia., 85(2):198-216 (2019).
Cranwell et al., Treatment of alopecia areata: An Australian expert consensus statement, Australas J. Dermatol., 60(2):163-70 (2019).
Cunha et al., Chronic Administration of Cannabidiol to Healthy Volunteers and Epileptic Patients, Pharmacology, 21(3):175-85 (1980).
Darwin et al., Alopecia Areata: Review of Epidemiology, Clinical Features, Pathogenesis, and New Treatment Options, Int. J. Trichology, 10(2):51-60 (2018).
Dermatology Aao, Alopecia areata: American Academy of Dermatology, (2018).
Dhital et al., Cannabidiol (CBD) induces functional Tregs in response to low-level T cell activation, Cell. Immunol., 312:25-34 (2017).
Foundation NAA, What you need to know about alopecia areata National Alopecia Areata Foundation (2019).
Gilhar et al., Alopecia Areata, N. Engl. J. Med., 366(16):1515-25 (2012).

(Continued)

*Primary Examiner* — Mark V Stevens
(74) *Attorney, Agent, or Firm* — MARSHALL, GERSTEIN & BORUN LLP

(57) ABSTRACT

Disclosed herein are topical formulations of cannabidiol, such as nanoparticulate cannabidiol, methods of making such compositions, and their use in treating autoimmune diseases and disorders, e.g., alopecia areata.

18 Claims, 6 Drawing Sheets

(56) References Cited

OTHER PUBLICATIONS

Hamed et al., Alopecia areata patients show deficiency of FOXP3+ CD39+ T regulatory cells and clonotypic restriction of Treg TCRß-chain, which highlights the immunopathological aspect of the disease, PLoS One, 14(7):e0210308 (2019).
Hammell et al., Transdermal cannabidiol reduces inflammation and pain-related behaviours in a rat model of arthritis, Eur. J. Pain, 20(6):936-48 (2016).
Han et al., Imbalance of T-helper 17 and regulatory T cells in patients with alopecia areata, J. Dermatol., 42(10):981-8 (2015).
Hessler et al., Artificial Intelligence in Drug Design, Molecules, 23(10):2520 (2018).
International Application No. PCT/US2021/021182, International Preliminary Report on Patentability, mailed Sep. 15, 2022.
International Application No. PCT/US2021/021182, International Search Report and Written Opinion, mailed May 20, 2021.
Kalekar et al., Regulatory T cells in inflammatory skin disease: from mice to humans, Int. Immunol., 31(7):457-63 (2019).
Kaplan et al., The profile of immune modulation by cannabidiol (CBD) involves deregulation of nuclear factor of activated T cells (NFAT), Biochem. Pharmacol., 76(6):726-37 (2008).
Katchan et al., Cannabinoids and autoimmune diseases: A systematic review, Autoimmun Rev., 15(6):513-28 (2016).
Korta et al., Alopecia areata is a medical disease, J. Am. Acad. Dermatol., 78(4):832-4 (2018).
Kozela et al., Cannabidiol inhibits pathogenic T cells, decreases spinal microglial activation and ameliorates multiple sclerosis-like disease in C57BL/6 mice, Br. J. Pharmacol., 163(7):1507-19 (2011).
Lodzki et al., Cannabidiol-transdermal delivery and anti-inflammatory effect in a murine model, J. Control Release, 93(3):377-87 (2003).
Maherani et al., Liposomes: A Review of Manufacturing Techniques and Targeting Strategies, Current Nanoscience, 7:436-452 (2011).
Malfait et al., The nonpsychoactive cannabis constituent cannabidiol is an oral anti-arthritic therapeutic in murine collagen-induced arthritis, Proc. Natl. Acad. Sci. U.S.A., 97(17):9561-6 (2000).
Mecha et al., Cannabidiol provides long-lasting protection against the deleterious effects of inflammation in a viral model of multiple sclerosis: a role for A2A receptors, Neurobiol. Dis., 59:141-50 (2013).
Mechoulam et al., Cannabidiol—Recent Advances, Chem. Biodivers, 4(8):1678-92 (2007).
Mechoulam et al., Cannabidiol: an overview of some pharmacological aspects, J. Clin. Pharmacol., 42(S1):11S-19S (2002).
Millar et al., A Systematic Review on the Pharmacokinetics of Cannabidiol in Humans, Front. Pharmacol., 9:1365 (2018).
Peyravian et al., Opioid antagonists as potential therapeutics for ischemic stroke, Prog. Neurobiol., 182:101679 (2019).
Pisanti et al., Cannabidiol: State of the art and new challenges for therapeutic applications, Pharmacol. Ther., 175:133-50 (2017).
Pratt et al., Alopecia areata, Nat. Rev. Dis. Primers., 3:17011 (2017).
Shapiro, Current Treatment of Alopecia Areata, J. Investig Dermatol. Symp. Proc., 16(1):S42-4 (2013).
Speiser et al., Regulatory T-cells in alopecia areata, J. Cutan Pathol., 46(9):653-8 (2019).
Strazzulla et al., Alopecia areata: An appraisal of new treatment approaches and overview of current therapies, J. Am. Acad. Dermatol., 78(1):15-24 (2018).
Stukelj et al., Synthesis of Stable Cannabidiol (CBD) Nanoparticles in Suspension, Mat. Technog., 53(4):543-549 (2019).
Weiss et al., Cannabidiol lowers incidence of diabetes in non-obese diabetic mice, Autoimmunity, 39(2):143-51 (2006).

* cited by examiner

Control

CBD

Minoxidil

CBD + Minoxidil

CANNABIDIOL NANODRUG FORMULATIONS AND METHODS FOR USE OF THE SAME

CROSS-REFERENCE TO RELATED APPLICATIONS

This is a U.S. National Phase of International Application No. PCT/US2021/021182, filed Mar. 5, 2021, which claims priority to U.S. Ser. No. 62/985,529, filed Mar. 5, 2020, and U.S. Ser. No. 63/055,038, filed Jul. 22, 2020, the respective disclosures of which are each incorporated herein by reference in their entireties.

BACKGROUND OF THE INVENTION

Field of the Invention

The present disclosure relates to formulations of cannabidiol, such as nanodrug formulations of cannabidiol, and their use in treating and preventing diseases, such as autoimmune disorders.

Description of Related Technology

Cannabidiol (CBD) is a non-psychoactive cannabinoid found in *Cannabis sativa*. In recent years, CBD has gained widespread publicity and been explored for its anti-inflammatory and immunomodulatory pharmacological properties as a natural and safe therapeutic option for autoimmune disorders including multiple sclerosis (MS), type 1 diabetes, and rheumatoid arthritis. Unlike CBD's psychoactive congener, $\Delta^9$-tetrahydrocannabinol (THC), CBD does not have a high affinity for either cannabinoid receptor, $CB_1$ or $CB_2$. Hence, CBD does not induce the psychoactive "high" often associated with THC. While the pharmacodynamics of CBD remain unclear, there is a strong precedent for the immunosuppressive properties of CBD. The immunomodulatory effects of CBD are thought to involve the suppression of lymphocyte proliferation, activation, and migration as well as inflammatory cytokine and chemokine production.

The immunomodulatory effects of CBD have been studied in various autoimmune disorders. For example, CBD has been found to inhibit T cell proliferation in autoimmune encephalomyelitis mice as a model of multiple sclerosis (MS), and the immunomodulatory therapeutic potential of CBD has also been shown for autoimmune joint destruction in an in vivo model of rheumatoid arthritis. However, the immunomodulatory effects of CBD have yet to be scientifically explored in the context of alopecia areata (AA), one of the most common autoimmune disorders. T regulatory cells ($T_{regs}$) are down-regulated in AA and involved in hair follicle immune privilege and AA pathogenesis. CBD has been shown to upregulate the expression of $T_{regs}$. Accordingly, the use of CBD as a therapeutic agent for immunomodulation is a novel and unexplored therapeutic avenue for treatment of AA.

Nearly 40% of drug molecules have failed in the drug development pipeline due to low solubility and bioavailability. Nanotechnology is a comprehensive drug discovery technique to overcome the poor solubility and low bioavailability of lipophilic drugs. In order to improve CBD drug delivery for more efficient and applicable AA therapeutic purposes, it is desirable to develop a formulation for non-invasive, direct and targeted delivery to the skin while avoiding issues associated with current delivery methods. Oral delivery of CBD is very inefficient with low bioavailability and extensive first pass metabolism. Alternatively, transdermal administration of CBD overcomes the drawbacks of oral delivery and increases patient comfort and compliance due to ease of self-application; however, current transdermal administrations of CBD are also insufficient in many ways due to the low permeability of the skin, in turn decreasing the absorption of the drug, and its respective pharmacological effects. This deficiency in transdermal administration of CBD can be attributed not only to the highly selective barrier nature of the human skin, but also the highly lipophilic nature of CBD, resulting in its accumulation within the upper layer of the skin, in turn, reducing penetration to deeper layers of the skin. Therefore, there is a need for transdermal delivery methods which enhance drug delivery, efficacy, passage, and permeation of CBD through the skin.

SUMMARY OF THE INVENTION

In one aspect, the disclosure relates to topical compositions comprising: (a) cannabidiol; and (b) a pharmaceutically acceptable carrier, wherein the cannabidiol is capable of penetrating into the skin.

In another aspect, the disclosure relates to topical compositions comprising: (a) nanoparticulate cannabidiol having an average particle size of about 5 nm to about 1000 nm; and (b) a pharmaceutically acceptable carrier, wherein the nanoparticulate cannabidiol is capable of penetrating into the skin.

In another aspect, the disclosure relates to topical compositions comprising: (a) cannabidiol; (b) minoxidil; and (c) a pharmaceutically acceptable carrier comprising ethanol, propylene glycol, and water, wherein the cannabidiol is capable of penetrating into the skin.

In another aspect, the disclosure relates to methods of treating or preventing a disease or disorder in a subject, comprising administering to the subject a therapeutically effective amount of the topical compositions disclosed herein. In some aspects, the disclosure relates to methods of treating or preventing alopecia areata.

Also disclosed are methods of preparing nanoparticulate cannabidiol comprising the steps of: (a) dissolving cannabidiol in a solvent to form a first solution; (b) admixing the first solution with an antisolvent that is miscible with the solvent to form a second solution; and (c) mixing the second solution at a rate in a range of about 300 to about to 5,000 rpm.

Further aspects and advantages will be apparent to those of ordinary skill in the art from a review of the following detailed description, taken in conjunction with the drawings. While the compounds and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION OF THE INVENTION

Figure 1:
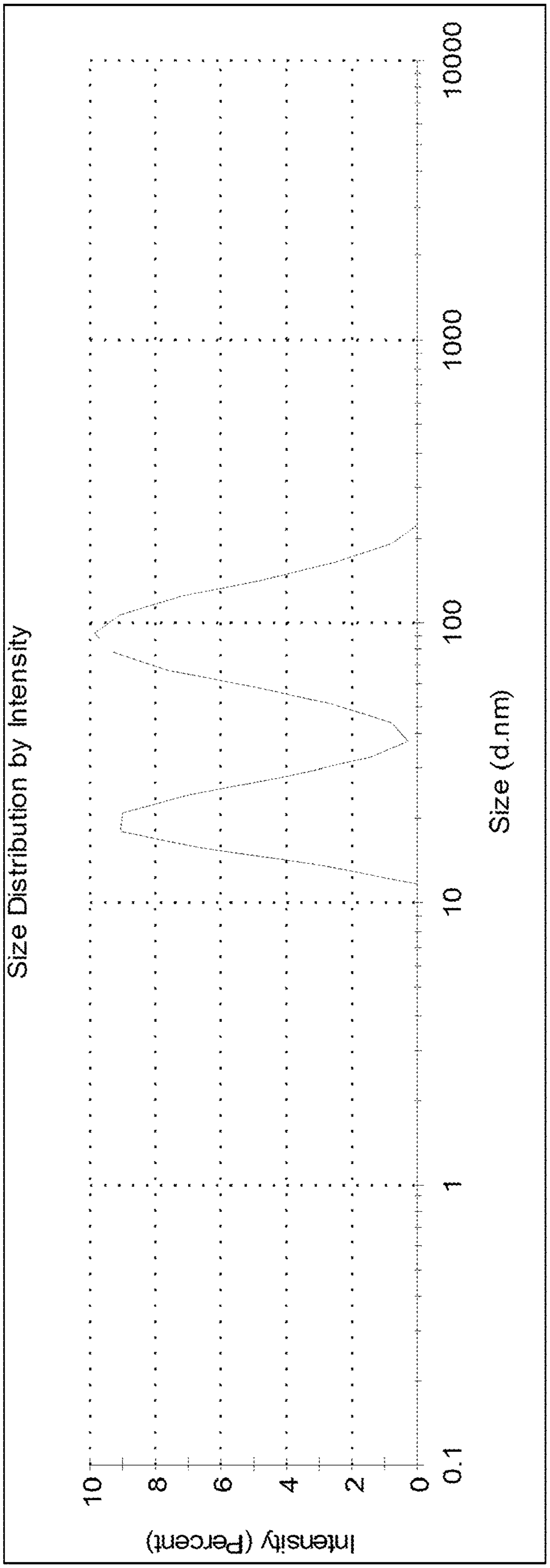
FIG. 1 depicts the hydrodynamic size of nanoparticulate cannabidiol as determined by dynamic light scattering, showing small, bimodal CBD nanoparticle size between 10 and 100 nm.

Provided herein are topical compositions comprising: (a) cannabidiol; and (b) a pharmaceutically acceptable carrier, wherein the cannabidiol is capable of penetrating into the skin. Also provided herein are topical compositions comprising: (a) nanoparticulate cannabidiol having an average particle size of about 5 nm to about 1000 nm; and (b) a pharmaceutically acceptable carrier, wherein the nanoparticulate cannabidiol is capable of penetrating into the skin. Cannabidiol is a compound having a structure:

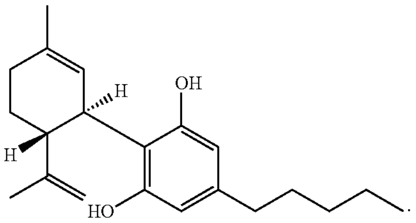 [SMILES: C=C(C)[C@@H]1CCC(C)=C[C@H]1c1c(O)cc(CCCCC)cc1O]

As used herein, "nanoparticulate cannabidiol" refers to nanoparticles of substantially pure cannabidiol (e.g., about 90%, 95%, 97%, 98%, 99%, 99.5%, or 100% pure by weight). The nanoparticles can have any shape conventionally used or known in the art, such as spheres, cubes, rods, and the like. In some embodiments, the nanoparticles are spheres or rods. In some embodiments, the nanoparticles are spheres. In various embodiments, the nanoparticles are rods. The nanoparticles are typically less than 1 μM in size. In some cases, the nanoparticles are less than 100 nm in size. In some cases, the nanoparticles are less than 50 nm in size. The topical composition provided herein are useful in the treatment of autoimmune diseases, such as alopecia areata (AA). Currently, there are no FDA-approved treatments for AA. Existing therapeutics of corticosteroids, topical immunotherapies, and immunosuppressants are insufficient in many ways; not only are they non-specific and neither curative nor preventive, but response rates from current treatments remain low with high relapse rates and susceptibility to adverse side effects. Non-specific broad immunosuppressants administered systematically or locally require strict patient follow-up and may even lead to fatal immunosuppression. Topical and intralesional corticosteroids may cause additional skin related side effects such as skin atrophy or telangiectasia. On the other hand, oral corticosteroids are only prescribed for short-term use as they are often associated with weight gain, adrenal gland suppression, and acne. The topical compositions provided herein advantageously allow the transport of cannabidiol through the skin. The topical compositions provided herein have improved bioavailability and avoid the first-pass metabolism associated with orally-administered cannabidiol. The topical compositions provided herein advantageously improve penetration of CBD into deeper layers of the skin compared to conventional topical CBD compositions, resulting in decreased amount and frequency of dosage. Consequently, the topical compositions provided herein are a safe and efficacious therapy to target the underlying immunomodulation in AA.

In some cases, the nanoparticulate cannabidiol has an average particle size of about 5 nm to about 200 nm. In some cases, the nanoparticulate cannabidiol has an average particle size of about 10 nm to about 100 nm. In some cases, the nanoparticulate cannabidiol has an average particle size of about 5 nm. In some cases, the nanoparticulate cannabidiol has an average particle size of about 10 nm. In some cases, the nanoparticulate cannabidiol has an average particle size of about 15 nm. In some cases, the nanoparticulate cannabidiol has an average particle size of about 20 nm. In some cases, the nanoparticulate cannabidiol has an average particle size of about 25 nm. In some cases, the nanoparticulate cannabidiol has an average particle size of about 30 nm. In some cases, the nanoparticulate cannabidiol has an average particle size of about 40 nm. In some cases, the nanoparticulate cannabidiol has an average particle size of about 50 nm. In some cases, the nanoparticulate cannabidiol has an average particle size of about 60 nm. In some cases, the nanoparticulate cannabidiol has an average particle size of about 70 nm. In some cases, the nanoparticulate cannabidiol has an average particle size of about 80 nm. In some cases, the nanoparticulate cannabidiol has an average particle size of about 90 nm. In some cases, the nanoparticulate cannabidiol has an average particle size of about 100 nm. In some cases, the nanoparticulate cannabidiol has an average particle size of about 110 nm. In some cases, the nanoparticulate cannabidiol has an average particle size of about 120 nm. In some cases, the nanoparticulate cannabidiol has an average particle size of about 130 nm. In some cases, the nanoparticulate cannabidiol has an average particle size of about 140 nm. In some cases, the nanoparticulate cannabidiol has an average particle size of about 150 nm. In some cases, the nanoparticulate cannabidiol has an average particle size of about 160 nm. In some cases, the nanoparticulate cannabidiol has an average particle size of about 170 nm. In some cases, the nanoparticulate cannabidiol has an average particle size of about 180 nm. In some cases, the nanoparticulate cannabidiol has an average particle size of about 190 nm. In some cases, the nanoparticulate cannabidiol has an average particle size of about 200 nm.

In some cases, the nanoparticulate cannabidiol exhibits a degree of monodispersity. In some cases, the nanoparticulate cannabidiol has greater than 75% uniformity in size distribution. In some cases, the nanoparticulate cannabidiol has greater than 80% uniformity in size distribution. In some cases, the nanoparticulate cannabidiol has greater than 85% uniformity in size distribution. In some cases, the nanoparticulate cannabidiol has greater than 90% uniformity in size distribution. In some cases, the nanoparticulate cannabidiol has greater than 95% uniformity in size distribution. In some cases, the nanoparticulate cannabidiol has greater than 98% uniformity in size distribution. In some cases, the nanoparticulate cannabidiol has greater than 99% uniformity in size distribution. In some cases, the nanoparticulate cannabidiol has 100% uniformity in size distribution.

In some cases, the nanoparticulate cannabidiol is substantially free of lipid or polymeric nanocarriers. As used herein, "substantially free" refers to a nanoparticulate cannabidiol having 1% or less, 0.5% or less, 0.4% or less, 0.3% or less, 0.2% or less, or 0.1% or less, 0.01% or less, or 0.001% or less, or 0% by weight of lipid or polymeric nanocarriers. As used herein a "lipid or polymeric nanocarrier" refers to any lipid or nanocarrier known to a skilled artisan and typically used in the art for preparing nanoformulations. Lipid or polymeric nanocarriers can comprise lipids, polymers, and/or non-polymer molecules, and combinations thereof. Such nanocarriers can be macromolecular. Lipid or polymeric nanocarriers can be, but are not limited to, one or a plurality of lipid-based nanoparticles, polymeric nanoparticles, surfactant-based emulsions, dendrimers, and/or nanoparticles that are developed using a combination of nanomaterials such as lipid-polymer nanoparticles. In some embodiments, the lipid nanocarriers are liposomes. Liposomes can comprise a lipid bilayer with amphiphilic properties, i.e., both interior and exterior surfaces of the bilayer are hydrophilic, and the bilayer lumen is hydrophobic. Lipophilic molecules, e.g., CBD, can spontaneously embed themselves into liposome membrane and retain their hydrophilic domains outside. and hydrophilic molecules can be chemically conjugated to the outer surface of liposome. Non-limiting examples of lipids include phosphatidylcholine, lipid A, cholesterol, dolichol, sphingosine, sphingomyelin, ceramide, glycosylceramide, cerebroside, sulfatide, phytosphingosine, phosphatidylethanolamine, phosphatidylglycerol, phosphatidylinositol, phosphatidylserine, cardiolipin, phosphatidic acid, and lyso-phophatides, and combinations thereof. Non-limiting examples of polymer nanocarriers include nanocarriers comprising polyethylene glycol (PEG), polyethylene oxide (PEO), polyalkylene glycol, and polyalkylene oxide, or biodegradable polymers such as polylactic acid (PLA), poly(glycolic acid) (PGA), and poly(lactic acid/glycolic acid) (PLGA), and combinations thereof, e.g., PEG-PLGA polymers. In some cases, the nanoparticulate cannabidiol contains 1% or less, 0.5% or less, 0.1% or less, 0.01% or less, or 0.001% or less by weight of lipid or polymeric nanocarriers. In some cases, the nanoparticulate cannabidiol contains 0.1% or less weight of lipid or polymeric nanocarriers. In some cases, the nanoparticulate cannabidiol contains 0.01% or less by weight of lipid or polymeric nanocarriers. In some cases, the nanoparticulate cannabidiol contains 0.001% or less by weight of lipid or polymeric nanocarriers.

In some cases, the nanoparticulate cannabidiol comprises at least 85% by weight of cannabidiol. In some cases, the nanoparticulate cannabidiol comprises at least 90% by weight of cannabidiol. In some cases, the nanoparticulate cannabidiol comprises at least 95% by weight of cannabidiol. In some cases, the nanoparticulate cannabidiol comprises at least 96% by weight of cannabidiol. In some cases, the nanoparticulate cannabidiol comprises at least 97% by weight of cannabidiol. In some cases, the nanoparticulate cannabidiol comprises at least 98% by weight of cannabidiol. In some cases, the nanoparticulate cannabidiol comprises at least 99% by weight of cannabidiol. In some cases, the nanoparticulate cannabidiol comprises at least 99.9% by weight of cannabidiol. In some cases, the nanoparticulate cannabidiol comprises 100% by weight of cannabidiol.

In some cases, the cannabidiol is present in the topical composition at a concentration of about 0.01 μg/mL to about 1 mg/mL. In some cases, the cannabidiol is present in the topical composition at a concentration of about 1 μg/mL to about 500 μg/mL. In some cases, the cannabidiol is present in the topical composition at a concentration of about 1 μg/mL to about 400 μg/mL. In some cases, the cannabidiol is present in the topical composition at a concentration of about 1 μg/mL to about 300 μg/mL. In some cases, the cannabidiol is present in the topical composition at a concentration of about 1 μg/mL to about 200 μg/mL. In some cases, the cannabidiol is present in the topical composition at a concentration of about 1 μg/mL to about 100 μg/mL. In some cases, the cannabidiol is present in the topical composition at a concentration of about 0.01 μg/mL to about 0.1 μg/mL. In some cases, the cannabidiol is present in the topical composition at a concentration of about 0.1 μg/mL to about 1 μg/mL. In some cases, the cannabidiol is present in the topical composition at a concentration of about 1 μg/mL to about 10 μg/mL. In some cases, the cannabidiol is present in the topical composition at a concentration of about 10 μg/mL to about 100 μg/mL. In some cases, the cannabidiol is present in the topical composition at a concentration of about 100 μg/mL to about 200 μg/mL. In some cases, the cannabidiol is present in the topical composition at a concentration of about 10 μg/mL to about 300 μg/mL. In some cases, the cannabidiol is present in the topical composition at a concentration of about 10 μg/mL to about 400 μg/mL. In some cases, the cannabidiol is present in the topical composition at a concentration of about 10 μg/mL to about 500 μg/mL. In some cases, the cannabidiol is present in the topical composition at a concentration of about 100 μg/mL to about 1 mg/mL. In some cases, the cannabidiol is present in the topical composition at a concentration of about 0.01 μg/mL. In some cases, the cannabidiol is present in the topical composition at a concentration of about 0.1 μg/mL. In some cases, the cannabidiol is present in the topical composition at a concentration of about 1 μg/mL. In some cases, the cannabidiol is present in the topical composition at a concentration of about 10 μg/mL. In some cases, the cannabidiol is present in the topical composition at a concentration of about 100 μg/mL. In some cases, the cannabidiol is present in the topical composition at a concentration of about 200 μg/mL. In some cases, the cannabidiol is present in the topical composition at a concentration of about 300 μg/mL. In some cases, the cannabidiol is present in the topical composition at a concentration of about 400 μg/mL. In some cases, the cannabidiol is present in the topical composition at a concentration of about 500 μg/mL. In some cases, the cannabidiol is present in the topical composition at a concentration of about 1 mg/mL. In some cases, the cannabidiol of any of the preceding embodiments is nanoparticulate cannabidiol.

In some cases, the nanoparticulate cannabidiol is present in the topical composition at a concentration of about 1 μM to about 2 mM. In some cases, the nanoparticulate cannabidiol is present in the topical composition at a concentration of about 5 μM to about 2 mM. In some cases, the nanoparticulate cannabidiol is present in the topical composition at a concentration of about 1 μM to about 1 mM. In some cases, the nanoparticulate cannabidiol is present in the topical composition at a concentration of about 5 μM to about 1 mM. In some cases, the nanoparticulate cannabidiol is present in the topical composition at a concentration of about 1 μM to about 500 μM. In some cases, the nanoparticulate cannabidiol is present in the topical composition at a concentration of about 5 μM to about 500 μM. In some cases, the nanoparticulate cannabidiol is present in the topical composition at a concentration of about 1 μM to about 200 μM. In some cases, the nanoparticulate cannabidiol is present in the topical composition at a concentration of about 5 μM to about 200 μM. In some cases, the nanoparticulate cannabidiol is present in the topical composition at a concentration of about 1 μM to about 100 μM. In some cases, the nanoparticulate cannabidiol is present in the topical composition at a concentration of about 5 μM to about 100 μM. In some cases, the nanoparticulate cannabidiol is present in the topical composition at a concentration of about 1 μM to about 50 μM. In some cases, the nanoparticulate cannabidiol is present in the topical composition at a concentration of about 5 μM to about 50 μM. In some cases, the nanoparticulate cannabidiol is present in the topical composition at a concentration of about 10 μM to about 50 μM. In some cases, the nanoparticulate cannabidiol is present in the topical composition at a concentration of about 20 μM to about 50 μM. In some cases, the nanoparticulate cannabidiol is present in the topical composition at a concentration of about 30 μM to about 50 μM. In some cases, the nanoparticulate cannabidiol is present in the topical composition at a concentration of about 40 μM to about 50 μM. In some cases, the nanoparticulate cannabidiol is present in the topical composition at a concentration of about 5 μM to about 10 μM. In some cases, the nanoparticulate cannabidiol is present in the topical composition at a concentration of about 5 μM to about 20 μM. In some cases, the nanoparticulate cannabidiol is present in the topical composition at a concentration of about 5 μM to about 30 μM. In some cases, the nanoparticulate cannabidiol is present in the topical composition at a concentration of about 5 μM to about 40 μM. In some cases, the nanoparticulate cannabidiol is present in the topical composition at a concentration of about 5 μM. In some cases, the nanoparticulate cannabidiol is present in the topical composition at a concentration of about 10 μM. In some cases, the nanoparticulate cannabidiol is present in the topical composition at a concentration of about 15 μM. In some cases, the nanoparticulate cannabidiol is present in the topical composition at a concentration of about 20 μM. In some cases, the nanoparticulate cannabidiol is present in the topical composition at a concentration of about 25 μM. In some cases, the nanoparticulate cannabidiol is present in the topical composition at a concentration of about 30 μM. In some cases, the nanoparticulate cannabidiol is present in the topical composition at a concentration of about 35 μM. In some cases, the nanoparticulate cannabidiol is present in the topical composition at a concentration of about 40 μM. In some cases, the nanoparticulate cannabidiol is present in the topical composition at a concentration of about 45 μM. In some cases, the nanoparticulate cannabidiol is present in the topical composition at a concentration of about 50 μM. In some cases, the nanoparticulate cannabidiol is present in the topical composition at a concentration of about 100 μM. In some cases, the nanoparticulate cannabidiol is present in the topical composition at a concentration of about 500 μM. In some cases, the nanoparticulate cannabidiol is present in the topical composition at a concentration of about 1 mM. In some cases, the nanoparticulate cannabidiol is present in the topical composition at a concentration of about 2 mM.

In some cases, the pharmaceutically acceptable carrier is a nanosphere, nanoassembly, nanoaerosol, or nanomicelle. As used herein, a "nanosphere" refers to a zero-dimensional nanoprecipitate. As used herein, a "nanoassembly" refers to carriers formed by self-assembly. Self-assembly refers to the process of the formation of a carrier using components that will orient themselves in a predictable manner forming carriers predictably and reproducibly. In some embodiments, the carriers are formed using amphiphilic biomaterials which orient themselves with respect to one another to form carriers of predictable dimension, constituents, and placement of constituents. As used herein, a "nanoaerosol" refers to sprays comprising nanoparticulate components. As used herein, a "nanomicelle" refers to nanocarriers comprising surfactants in an aqueous carrier. In some cases, the pharmaceutically acceptable carrier is a nanosphere. In some cases, the pharmaceutically acceptable carrier is a nanoassembly. In some cases, the pharmaceutically acceptable carrier is a nanoaerosol. In some cases, the pharmaceutically acceptable carrier is a nanomicelle.

In some cases, the pharmaceutically acceptable carrier comprises ethanol. In some cases, the pharmaceutically acceptable carrier comprises propylene glycol. In some cases, the pharmaceutically acceptable carrier comprises water. In some cases, the pharmaceutically acceptable carrier comprises ethanol, propylene glycol, and water.

In some cases, the cannabidiol is capable of penetrating into the epidermis. In some cases, the nanoparticulate cannabidiol is capable of penetrating into the epidermis. As used herein, the phrase "capable of penetrating into the epidermis" refers to a cannabidiol or nanoparticulate cannabidiol that permeates through the surface of the skin, no deeper than the basal layer of the skin. In some cases, the cannabidiol is capable of penetrating into the dermis. In some cases, the nanoparticulate cannabidiol is capable of penetrating into the dermis. As used herein, the phrase "capable of penetrating into the dermis" refers to a cannabidiol or nanoparticulate cannabidiol that permeates through the surface of the skin, no deeper than the reticular layer of the skin.

Also disclosed are topical compositions comprising cannabidiol and another therapeutic agent. Further disclosed are topical compositions comprising nanoparticulate cannabidiol and another therapeutic agent. In some cases, the other therapeutic agent can treat or prevent hair loss. In some cases, the other therapeutic agent is an alopecia treatment. In some cases, the other therapeutic is a 5α-reductase inhibitor, antiandrogen, or a potassium channel opener. In some cases, the 5α-reductase inhibitor is alfatradiol, dutasteride, finasteride, or saw palmetto extract. In some cases, the antiandrogen is bicalutamide, cyproterone acetate, flutamide, spironolactone, or topilutamide. In some cases, the potassium channel opener is minoxidil. In some cases, the other therapeutic is nepidermin. In some cases, the other therapeutic agent is minoxidil.

In some cases, the topical composition comprises about 0.01% to about 15% by weight of cannabidiol. In some cases, the topical composition comprises about 0.01% to about 1% by weight of cannabidiol. In some cases, the topical composition comprises about 1% to about 5% by weight of cannabidiol. In some cases, the topical composition comprises about 5% to about 10% by weight of cannabidiol. In some cases, the topical composition comprises about 10% to about 15% by weight of cannabidiol. In some cases, the topical composition comprises about 1% to about 15% by weight of minoxidil. In some cases, the topical composition comprises about 1% to about 5% by weight of minoxidil. In some cases, the topical composition comprises about 5% to about 10% by weight of minoxidil. In some cases, the topical composition comprises about 10% to about 15% by weight of minoxidil. In some cases, the topical composition comprises about 0.01% to about 15% by weight of cannabidiol and about 1% to about 15% by weight of minoxidil.

In some cases, the topical composition comprises about 0.01% to about 15% by weight of nanoparticulate cannabidiol. In some cases, the topical composition comprises about 0.01% to about 1% by weight of nanoparticulate cannabidiol. In some cases, the topical composition comprises about 1% to about 5% by weight of nanoparticulate cannabidiol. In some cases, the topical composition comprises about 5% to about 10% by weight of nanoparticulate cannabidiol. In some cases, the topical composition comprises about 10% to about 15% by weight of nanoparticulate cannabidiol. In some cases, the topical composition comprises about 1% to about 15% by weight of minoxidil. In some cases, the topical composition comprises about 1% to about 5% by weight of minoxidil. In some cases, the topical composition comprises about 5% to about 10% by weight of minoxidil. In some cases, the topical composition comprises about 10% to about 15% by weight of minoxidil. In some cases, the topical composition comprises about 0.01% to about 15% by weight of cannabidiol and about 1% to about 15% by weight of minoxidil. In some cases, the topical composition comprises about 0.01% to about 0.05% by weight of cannabidiol and about 1% to about 10% by weight of minoxidil. In some cases, the topical composition comprises about 0.02% by weight of cannabidiol and about 5% by weight of minoxidil.

Also disclosed are topical compositions comprising cannabidiol, minoxidil, and a pharmaceutically acceptable carrier, wherein the cannabidiol is capable of penetrating into the skin. In some embodiments, the pharmaceutically acceptable carrier comprises ethanol. In some embodiments, the pharmaceutically acceptable carrier comprises propylene glycol. In some embodiments, the pharmaceutically acceptable carrier comprises water. In some embodiments, the pharmaceutically acceptable carrier comprises ethanol, propylene glycol, and water. In some cases, the cannabidiol is present at a concentration of about 1 μM to about 2 mM. In some cases, the cannabidiol is present at a concentration of about 5 μM to about 2 mM. In some cases, the minoxidil is present at a concentration of about 0.01% to about 20% by weight. In some cases, the minoxidil is present at a concentration of about 0.01% to about 1% by weight. In some cases, the minoxidil is present at a concentration of about 1% to about 5% by weight. In some cases, the minoxidil is present at a concentration of about 2% to about 5% by weight. In some cases, the minoxidil is present at a concentration of about 5% to about 10% by weight. In some cases, the minoxidil is present at a concentration of about 10% to about 15% by weight. In some cases, the minoxidil is present at a concentration of about 15% to about 20% by weight. In some cases, the minoxidil is present at a concentration of about 1% to about 10% by weight. In some cases, the minoxidil is present at a concentration of about 10% to about 20% by weight. In some cases, the minoxidil is present at a concentration of about 2% by weight. In some cases, the minoxidil is present at a concentration of about 5% by weight.

In some cases, the cannabidiol and minoxidil are present in a ratio of about 0.01:1 to 1,000,000:10. In some cases, the cannabidiol and minoxidil are present in a ratio of about 0.01:1 to 1,000,000:1. In some cases, the cannabidiol and minoxidil are present in a ratio of about 0.01:1 to 0.1:1. In some cases, the cannabidiol and minoxidil are present in a ratio of about 0.1:1 to 1:1. In some cases, the cannabidiol and minoxidil are present in a ratio of about 1:1 to 10:1. In some cases, the cannabidiol and minoxidil are present in a ratio of about 10:1 to 100:1. In some cases, the cannabidiol and minoxidil are present in a ratio of about 100:1 to 1,000:1. In some cases, the cannabidiol and minoxidil are present in a ratio of about 1,000:1 to 10,000:1. In some cases, the cannabidiol and minoxidil are present in a ratio of about 10,000:1 to 100,000:1. In some cases, the cannabidiol and minoxidil are present in a ratio of about 100,000:1 to 1,000,000:10. In some cases, the cannabidiol and minoxidil are present in a ratio of about 0.01:1 to 1,000,000:1.

A skilled artisan will be able to choose an appropriate concentration of minoxidil in the disclosed compositions based on a characteristic of the patient to be treated and/or the desired effect. For example, in some cases, the minoxidil is present at a concentration of about 2% by weight in topical compositions for use in treating female patients, and in some cases, the minoxidil is present at a concentration of about 5% by weight in topical compositions for use in treating male patients.

Also provided are methods of preparing nanoparticulate cannabidiol. In some cases, the method comprises the steps of:

(a) dissolving cannabidiol in a solvent to form a first solution;

(b) admixing the first solution with an antisolvent that is miscible with the solvent to form a second solution; and (c) mixing the second solution at a rate in a range of about 300 to about to 5,000 rpm.

In some cases, the solvent is a polar solvent, such as a polar protic or polar aprotic solvent. Suitable protic alcohol solvents include, for example, methanol, ethanol, n-propanol, isopropanol, n-butanol, sec-butanol, and tert-butanol. Suitable aprotic solvents include, for example, acetonitrile, dimethyl sulfoxide, dimethyl formamide, N-methylpyrrolidine, pyridine, ethyl acetate, and hexamethylphosphoramide. In some cases, the solvent is methanol, ethanol, or acetonitrile. In some cases, the solvent is methanol. In some cases, the solvent is ethanol. In some cases, the solvent is acetonitrile.

In some cases, the cannabidiol is present in the first solution in a concentration in a range of about 1 μM to about 20 mM. In some cases, the cannabidiol is present in the first solution in a concentration in a range of about 1 μM to about 10 mM. In some cases, the cannabidiol is present in the first solution in a concentration in a range of about 1 μM to about 10 μM. In some cases, the cannabidiol is present in the first solution in a concentration in a range of about 1 μM to about 50 μM. In some cases, the cannabidiol is present in the first solution in a concentration in a range of about 40 μM to about 20 mM. In some cases, the cannabidiol is present in the first solution in a concentration in a range of about 40 μM to about 50 μM. In some cases, the cannabidiol is present in the first solution in a concentration in a range of about 40 μM to about 50 μM. In some cases, the cannabidiol is present in the first solution in a concentration in a range of about 50 OA to about 100 μM. In some cases, the cannabidiol is present in the first solution in a concentration in a range of about 100 μM to about 500 μM. In some cases, the cannabidiol is present in the first solution in a concentration in a range of about 500 μM to about 1 mM. In some cases, the cannabidiol is present in the first solution in a concentration in a range of about 1 mM to about 5 mM. In some cases, the cannabidiol is present in the first solution in a concentration in a range of about 5 mM to about 10 mM. In some cases, the cannabidiol is present in the first solution in a concentration in a range of about 1 mM to about 5 mM. In some cases, the cannabidiol is present in the first solution in a concentration in a range of about 5 mM to about 10 mM. In some cases, the cannabidiol is present in the first solution in a concentration in a range of about 10 mM to about 15 mM. In some cases, the cannabidiol is present in the first solution in a concentration in a range of about 15 mM to about 20 mM. In some cases, the cannabidiol is present in the first solution in a concentration of about 1 μM. In some cases, the cannabidiol is present in the first solution in a concentration of about 10 μM. In some cases, the cannabidiol is present in the first solution in a concentration of about 20 μM. In some cases, the cannabidiol is present in the first solution in a concentration of about 30 μM. In some cases, the cannabidiol is present in the first solution in a concentration of about 40 μM. In some cases, the cannabidiol is present in the first solution in a concentration of about 50 μM. In some cases, the cannabidiol is present in the first solution in a concentration of about 60 μM. In some cases, the cannabidiol is present in the first solution in a concentration of about 70 μM. In some cases, the cannabidiol is present in the first solution in a concentration of about 80 μM. In some cases, the cannabidiol is present in the first solution in a concentration of about 90 μM. In some cases, the cannabidiol is present in the first solution in a concentration of about 100 μM. In some cases, the cannabidiol is present in the first solution in a concentration of about 200 μM. In some cases, the cannabidiol is present in the first solution in a concentration of about 500 μM. In some cases, the cannabidiol is present in the first solution in a concentration of about 1 mM. In some cases, the cannabidiol is present in the first solution in a concentration of about 2 mM. In some cases, the cannabidiol is present in the first solution in a concentration of about 3 mM. In some cases, the cannabidiol is present in the first solution in a concentration of about 4 mM. In some cases, the cannabidiol is present in the first solution in a concentration of about 5 mM. In some cases, the cannabidiol is present in the first solution in a concentration of about 10 mM. In some cases, the cannabidiol is present in the first solution in a concentration of about 10 mM. In some cases, the cannabidiol is present in the first solution in a concentration of about 20 mM.

In some cases, the antisolvent comprises water. In some cases, the antisolvent is water. In some cases, the antisolvent comprises water and a surfactant. In some cases, the surfactant is nonionic, cationic, or anionic. In some cases, the surfactant is a polysorbate. In some cases, the surfactant is polysorbate 20, polysorbate 40, polysorbate 60, polysorbate 80, or combinations thereof. In some cases, the surfactant is polysorbate 20. In some cases, the surfactant comprises Triton X-100. In some cases, the surfactant is selected from the group consisting of polysorbate 20, polysorbate 40, polysorbate 60, polysorbate 80, Triton X-100, and combinations thereof. In some cases, the antisolvent comprises water and polysorbate 20.

In some cases, the solvent is selected from the group consisting of methanol, ethanol, and acetonitrile and the antisolvent is water or water and a surfactant, as previously described herein. In some cases, the solvent is methanol and the antisolvent comprises water. In some cases, the solvent is methanol and the antisolvent is water.

In some cases, the ratio of the first solution to the antisolvent is in a range of about 1:10 to about 1:1000 by volume. In some cases, the ratio of the first solution to the antisolvent is in a range of about 1:10 to about 1:500 by volume. In some cases, the ratio of the first solution to the antisolvent is in a range of about 1:10 to about 1:400 by volume. In some cases, the ratio of the first solution to the antisolvent is in a range of about 1:10 to about 1:300 by volume. In some cases, the ratio of the first solution to the antisolvent is in a range of about 1:10 to about 1:200 by volume. In some cases, the ratio of the first solution to the antisolvent is in a range of about 1:10 to about 1:100 by volume. In some cases, the ratio of the first solution to the antisolvent is about 1 to about 10 by volume. In some cases, the ratio of the first solution to the antisolvent is about 1 to about 20 by volume. In some cases, the ratio of the first solution to the antisolvent is about 1 to about 30 by volume. In some cases, the ratio of the first solution to the antisolvent is about 1 to about 40 by volume. In some cases, the ratio of the first solution to the antisolvent is about 1 to about 50 by volume. In some cases, the ratio of the first solution to the antisolvent is about 1 to about 60 by volume. In some cases, the ratio of the first solution to the antisolvent is about 1 to about 70 by volume. In some cases, the ratio of the first solution to the antisolvent is about 1 to about 80 by volume. In some cases, the ratio of the first solution to the antisolvent is about 1 to about 90 by volume. In some cases, the ratio of the first solution to the antisolvent is about 1 to about 100 by volume.

In some cases, the second solution is mixed at a rate in a range of about 300 to about 5000 rpm. In some cases, the second solution is mixed at a rate in a range of about 300 to about 2000 rpm. In some cases, the second solution is mixed at a rate in a range of about 300 to about 1000 rpm. In some cases, the second solution is mixed at a rate in a range of about 300 to about 500 rpm. In some cases, the second solution is mixed at a rate of about 300 rpm. In some cases, the second solution is mixed at a rate of about 400 rpm. In some cases, the second solution is mixed at a rate of about 500 rpm. In some cases, the second solution is mixed at a rate of about 1000 rpm. In some cases, the second solution is mixed at a rate of about 1100 rpm. In some cases, the second solution is mixed at a rate of about 1200 rpm. In some cases, the second solution is mixed at a rate of about 1300 rpm. In some cases, the second solution is mixed at a rate of about 1400 rpm. In some cases, the second solution is mixed at a rate of about 1500 rpm. In some cases, the second solution is mixed at a rate of about 2000 rpm. In some cases, the second solution is mixed at a rate of about 3000 rpm. In some cases, the second solution is mixed at a rate of about 4000 rpm. In some cases, the second solution is mixed at a rate of about 5000 rpm.

In some cases, the solvent is methanol, ethanol, or acetonitrile, the cannabidiol is present in the first solution in a concentration of about 1 μM to 100 mM, the antisolvent is water, the ratio of first solution to antisolvent is about 1:10 to 1:1000 by volume, and the second solution is mixed at a rate in a range of about 300 to about 2000 rpm. In some cases, the solvent is methanol, ethanol, or acetonitrile, the cannabidiol is present in the first solution in a concentration of about 20 μM to 50 mM, the antisolvent is water, the ratio of first solution to antisolvent is about 1:10 to 1:500 by volume, and the second solution is mixed at a rate in a range of about 300 to about 2000 rpm. In some cases, the solvent is methanol, ethanol, or acetonitrile, the cannabidiol is present in the first solution in a concentration of about 40 μM to 20 mM, the antisolvent is water, the ratio of first solution to antisolvent is about 1:10 to 1:400 by volume, and the second solution is mixed at a rate in a range of about 300 to about 2000 rpm. In some cases, the solvent is methanol, ethanol, or acetonitrile, the cannabidiol is present in the first solution in a concentration of about 1 μM to 100 μM, the antisolvent is water, the ratio of first solution to antisolvent is about 1:10 to 1:100 by volume, and the second solution is mixed at a rate in a range of about 300 to about 2000 rpm. In some cases, the solvent is methanol or acetonitrile, the cannabidiol is present in the first solution in a concentration of about 1 μM to 50 μM, the antisolvent is water, the ratio of first solution to antisolvent is about 1:25 to 1:75 by volume, and the second solution is mixed at a rate in a range of about 500 to about 1500 rpm. In some cases, the solvent is methanol or acetonitrile, the cannabidiol is present in the first solution in a concentration of about 1 μM to 100 mM, the antisolvent is water, the ratio of first solution to antisolvent is about 1:25 to 1:75 by volume, and the second solution is mixed at a rate in a range of about 500 to about 1500 rpm. In some cases, the solvent is methanol or acetonitrile, the cannabidiol is present in the first solution in a concentration of about 20 μM to 500 mM, the antisolvent is water, the ratio of first solution to antisolvent is about 1:25 to 1:75 by volume, and the second solution is mixed at a rate in a range of about 500 to about 1500 rpm. In some cases, the solvent is methanol or acetonitrile, the cannabidiol is present in the first solution in a concentration of about 40 μM to 20 mM, the antisolvent is water, the ratio of first solution to antisolvent is about 1:25 to 1:75 by volume, and the second solution is mixed at a rate in a range of about 500 to about 1500 rpm. In some cases, the solvent is methanol, the cannabidiol is present in the first solution in a concentration of about 10 OA, the antisolvent is water, the ratio of first solution to antisolvent is about 1:50 by volume, and the second solution is mixed at a rate in a range of about 1200 rpm. In some cases, the solvent is methanol, the cannabidiol is present in the first solution in a concentration of about 3 mM (e.g., 3.2 mM or 3.18 mM), the antisolvent is water, the ratio of first solution to antisolvent is about 1:50 by volume, and the second solution is mixed at a rate in a range of about 1200 rpm.

Additional synthetic procedures for preparing the nanoparticulate cannabidiol compositions disclosed herein can be found in the Examples section.

Methods of Using Nanoparticulate Cannabidiol Topical Compositions

The immunomodulatory effects of CBD have been studied in various autoimmune disorders. For example, CBD has been found to inhibit T cell proliferation in autoimmune encephalomyelitis mice as a model of MS. The long-term immunomodulatory effects of CBD in reduction of TNF-α and IL-1β for encephalomyelitis virus-induced demyelinating murine model of MS have been observed to be consistent with the acute effects, evidencing the potential for CBD as a long-term therapeutic agent for autoimmune diseases. Similarly, CBD has been shown to suppress T cell function through suppression of IL-2 and IFN-γ in (nuclear factor of activated T cells) NFAT activated T cells. The immunomodulatory therapeutic potential of CBD has also been shown for autoimmune joint destruction in an in vivo model of rheumatoid arthritis. Specifically, CBD was shown to be immunosuppressive by reducing tumor necrosis factor (TNF) and IFN-γ production in mice with collagen-induced arthritis (CIA). The immunomodulatory effects of CBD have been shown for type-1 diabetes. CBD-treated NOD (non-obese diabetic) mice were found to have significant reduction in Th-1 inflammatory cytokine production of IFN-γ and TNF-α, however an increase in Th2 cytokine production of IL-4 and IL-10 was observed. Without wishing to be bound by theory, this shows that CBD exerts an immunomodulatory mechanism resulting in a Th1 to Th2 immune response shift. In a similar study, CBD was once again shown to significantly reduce plasma levels of pro-inflammatory cytokine IFN-γ and TNF-α in NOD mice treated with CBD. These mice also exhibited a decrease in Th-1 cytokine production and increase production of Th2-associated cytokines IL-4 and IL-10. Without wishing to be bound by theory, these results once again show that CBD has an immunomodulatory role, shifting immune responses from Th1 to Th2. The immunosuppressive activity of CBD has also been exhibited through $T_{reg}$ induction, and CBD was found to stimulate $T_{regs}$ in response to low-level T cell stimulation. CBD therefore can be a favorable therapeutic option for autoimmune disorders to target immunomodulation, with minimal side effects and potential for long-term patient administration.

Alopecia areata (AA) is one of the most common autoimmune disorders, in which the immune system attacks hair follicles (HF) resulting in non-scarring hair loss in the form of patches on the scalp, entire scalp, or entire body. To date, the pathophysiology of AA is not clearly understood. While genetic and environmental factors were initially suggested to attribute to the onset of AA, insult to the HF immune privilege (IP) is more recently described as a plausible pathomechanism of AA. As a disease that affects nearly 7 million people in the US and approximately a 2% lifetime risk of AA development in the general population, AA significantly impact's the individuals' quality of life and self-esteem. Under normal physiological conditions, the HF is immune privileged, ultimately protecting the HF from autoantigens that can illicit an autoimmune response. The immunoinhibitory environment surrounding the HF suppresses presentation of autoantigens through expression of macrophage migration inhibitory factor (MIF), preventing infiltration of cytotoxic T lymphocytes. When the HF IP becomes compromised, however, the surrounding inflammatory immune cells, i.e. $CD4^+$ and $CD8^+$ lymphocytes stimulate an immune attack of the HF, consequently the presentation of AA. While initiation of a disturbed IP remains ambiguous, deficiency of T regulatory cells ($T_{regs}$) is suggested and has been observed clinically. $T_{regs}$ are crucial immune cells in preserving cutaneous homeostasis and IP by modulating immune response through prevention and protection of autoimmune responses against exogenous antigens. Accordingly, $T_{reg}$ dysregulation reduces this immune response inhibition, ultimately contributing to autoimmune disorder pathogenesis, including AA. The underlying mechanism for $T_{reg}$ disruption in AA, however, remains unclear.

As previously described, there are no FDA-approved treatments for AA. Concurrently, existing therapeutics of corticosteroids, topical immunotherapies, and immunosuppressants are insufficient in many ways; not only are they non-specific and neither curative nor preventive, but response rates from current treatments remains low with high relapse rates and susceptibility to adverse side effects. Non-specific broad immunosuppressants administered systematically or locally require strict patient follow-up and may even lead to fatal immunosuppression. Topical and intralesional corticosteroids may cause additional skin related side effects such as skin atrophy or telangiectasia. On the other hand, oral corticosteroids are only prescribed for short-term use as they often associated with weight gain, adrenal gland suppression, and acne. Consequently, the field is in need of novel, safe, and efficacious therapies to target the underlying immunomodulation in AA.

Many drug molecules have failed in the drug development pipeline due to low solubility and bioavailability. In order to improve CBD drug delivery for more efficient and applicable AA therapeutic purposes, it is desirable to develop a formulation for non-invasive, direct and targeted delivery to the skin while avoiding issues associated with current delivery methods. Current cannabinoid delivery systems include lipid-based or polymer-based nanoparticles, but pure cannabinoid nanodrugs have yet to be explored, let alone in the context of immunomodulation of AA.

Nanotechnology is attractive for improving both cannabinoid drug design and opening a novel avenue for CBD delivery through the skin due to the poor solubility, lipophilic, and low stability characteristics of cannabinoids as well as the difficulties association with drug transport through the skin. Synthesis of CBD into pure drug nanoparticles is a novel method to solve these solubility issues and allow for novel drug delivery avenues. CBD nanodrugs are expected to maintain innate therapeutic and non-toxic properties of original drugs. Simultaneously, the reduced particle size and decreased diffusion distance is expected to not only enhance drug absorption through the skin barrier and in turn promote efficacious modulation of the immune system, but also to decrease the dosage and frequency of dosage required for the patient.

Methods of Treating Autoimmune Diseases

The CBD formulations of the disclosure (e.g., the CBD nanoparticle formulations and the non-nanoparticle CBD formulations) are effective in the reduction of T-lymphocytes (see FIGS. 1-4), and can be used as effective immune modulators alone, as well as in combination with an additional therapeutic agent, such as minoxidil, Accordingly, disclosed herein are methods of treating or preventing a disease or disorder in a subject, comprising administering to the subject a therapeutically effective amount of a cannabidiol topical composition, such as a nanoparticulate cannabidiol topical composition, described herein. In some cases, the disease or disorder is an autoimmune disease or disorder. In some cases, the disease or disorder is alopecia areata.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a composition of the disclosure to an individual in need of such treatment. Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be affected over a short period, be oriented over a medium term, or can be a long-term treatment, for example within the context of a maintenance therapy. As used herein, the terms "prevent," "preventing," and "prevention," are art-recognized, and when used in relation to a condition, such as alopecia areata, is well understood in the art, and includes administration of a composition which reduces the frequency of, or delays the onset of, symptoms of a medical condition in a subject relative to a subject which does not receive the composition. Thus, prevention of alopecia areata includes, for example, reducing inflammation, restoring or enhancing immune privilege of hair follicles, or reducing the levels of T cell lymphocytes near hair follicles in a treated population versus an untreated control population, e.g., by a statistically and/or clinically significant amount.

In some cases, the methods disclosed herein comprise treating or preventing hair loss. In some cases, the methods disclosed herein comprise treating hair loss. In some cases, the methods disclosed herein comprise preventing hair loss.

In some cases, the methods disclosed herein comprise administering to the subject one or more additional pharmaceutically active agents. In some cases, the additional pharmaceutically active agent is a hair-growth stimulating agent. In some cases, the additional pharmaceutically active agent is an antihypertensive vasodilator, a 5-alpha reductase inhibitor, an immunosuppressant, a calcineurin modulator, or a Janus kinase (JAK) inhibitor. In some cases, the antihypertensive vasodilator is minoxidil. In some cases, the 5-alpha reductase inhibitor is simvastatin. In some cases, the immunosuppressant is a corticosteroid. In some cases, the corticosteroid is clobetasol or fluocinide. In some cases, the calcineurin modulator is cyclosporine or tacrolimus. In some cases, the JAK inhibitor is ruxolitinib, tofacitinib, or oclacitinib. In some cases, the additional pharmaceutically active agent is a corticosteroid. In some cases, the additional pharmaceutically active agent is simvastatin or minoxidil. In some cases, the additional pharmaceutically active agent is minoxidil.

With respect to the amount of cannabidiol or nanoparticulate cannabidiol incorporated in each topical formulation, the cannabidiol content will typically be adjusted such that when the topical formulation is applied to a treatment area of a subject in need thereof, the amount of compound for stimulating hair regrowth (i.e., for treating alopecia areata) is present in an amount effective to achieve at least one of: (i) activating the anagen phase in a hair follicle; (ii) inhibiting the hair follicle from entering the catagen phase; (iii) reverting the hair follicle from the catagen phase to the anagen phase; and (iv) promoting the hair follicle to enter the anagen phase from the telogen phase.

Uses of the topical compositions disclosed herein in the preparation of a medicament for treating the diseases and disorders described herein are provided.

Topical Formulations

Provided herein are topical formulations that include cannabidiol and one or more pharmaceutically acceptable carrier(s). Also provided herein are topical formulations that include the nanoparticulate cannabidiol of the disclosure, and one or more pharmaceutically acceptable carrier(s). The term "pharmaceutically acceptable carrier" refers to a medium that does not interfere with the effectiveness of the biological activity of the active ingredient(s) and is not toxic to the host to which it is administered.

Topical formulations disclosed herein may be formulated as creams, lotions, ointments, sprays, foams, or gels. Suitable formulations may further incorporate nanoparticulate cannabidiol in the form of micelles, liposomes, nanoparticles, or aerosols that encapsulate the nanoparticulate cannabidiol.

The disclosed cannabidiol and nanoparticulate cannabidiol can be encapsulated in cosmetically acceptable formulations, and especially formulations using a lipid membrane. For example, the cannabidiol and nanoparticulate cannabidiol can be included in micelles, nanomicelles, liposomes, microcapsules, nanocapsules, microparticles, nanoparticles, nanospheres, and nanoassemblies. A description of some cosmetically acceptable cosmetic delivery systems can be found in Maherani et al, "Liposomes: A Review of Manufacturing Techniques and Targeting Strategy," Current Nanoscience; 7:436-452 (2011). A method of liposome manufacturing is a shear method. Topical delivery systems resemble naturally occurring membranes, are flexible, and can penetrate interstitial spaces between cells. Topical delivery systems can have monolayer, bilayer (e.g. unilammellar vesicle or ULV), or multilayer structures (e.g. multilamellar vesicles or MLV). Additionally, multilayer liposomes, microcapsules, microsomes, and nanocapsules can have nested structures (e.g. multivesicular vesicle or MVV). Cannabidiol and nanoparticulate cannabidiol delivery systems used in the topical formulations can range in size from about 500 nm to about 10 μm. In the preparation of topical delivery systems, all topically acceptable lipid compositions are contemplated, especially pharmaceutically acceptable lipids. Topical delivery systems include amphipathic or amphiphilic molecules such as phospholipids or combinations of phospholipids (e.g., phosphatidylcholine, phosphatidylethanolamine, phosphatidic acid, phosphatidylserine, and phosphoinositides). Additionally, topical delivery systems can contain additives such as sterols, polyethylene glycol, cholesterol, dicethylphosphate, stearyl amine, and the like. Unilamellar vesicles/liposomes can be produced using high shear techniques.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like.

The compounds of the disclosure can be administered to a subject or patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

When a subject or patient is to receive or is receiving multiple pharmaceutically active agents, the agents can be administered simultaneously, or sequentially. For example, in the case of topical compositions, the active agents may be found in one topical composition or in separate topical compositions, which can be administered at once or sequentially in any order. In addition, it should be recognized that the compositions may be different forms. For example, one or more compound may be delivered via a tablet, while another is administered as a topical composition. All combinations, delivery methods and administration sequences are contemplated.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., topical application). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

Described in the below examples are syntheses of CBD formulations, such as CBD nanoparticle formulations, and methods for evaluating them for efficacy in modulating T-lymphocytes in an AA in vitro platform. This CBD nanoformulation, in particular, opens up a novel drug delivery avenue and serves as a promising immunomodulatory agent for treatment of AA and possibly other forms of Alopecia to ultimately improve the patient's quality of life through hair regrowth.

The following examples are provided for illustration and are not intended to limit the scope of the disclosure.

Example 1

CBD nanoparticles were formulated using a bottom reprecipitation technique that involves self-assembly of nanoparticles by drug molecules interacting and coming together through rapid mixing. The reprecipitation method follows the following steps: 1) dissolving the lipophilic drugs in an organic solvent to form an organic solution 2) mixing the organic solution in a large amount of anti-solvent that is miscible with the organic solvent 3) rapidly mixing the organic solution in anti-solvent to ensure fast nucleation, in turn particles that are small in size. Monodispersed nanoparticles were achieved through optimization of different variables including stirring speed, drug concentration, and type of solvent used.

Figure 2:
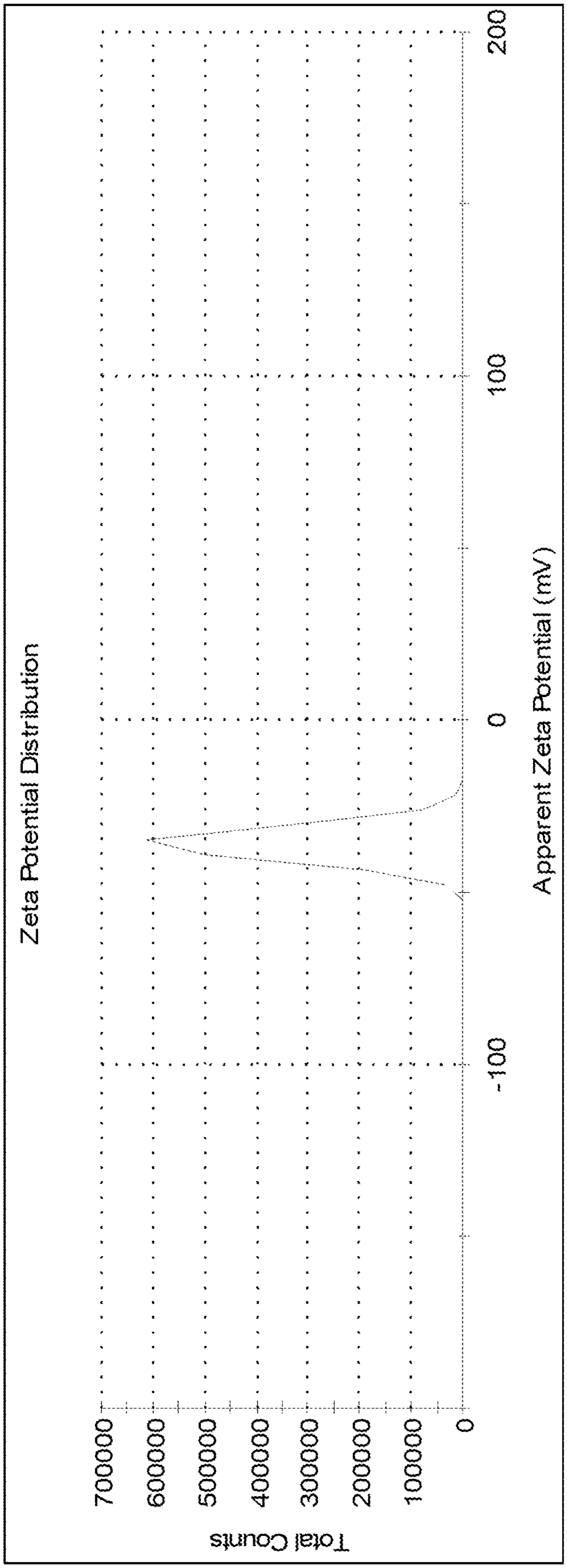
FIG. 2 depicts the stability of nanoparticulate cannabidiol as determined by Zeta g) potential, showing an electrical charge of approximately −30 mV that directly correlates with stable nanoparticle formulations.

Nanoparticles were characterized using Dynamic Light Scattering (DLS) and Zeta g) potential to determine the hydrodynamic size of the nanoparticle and stability of the nanoparticles, respectively. Small, bimodal CBD nanoparticle sizes between 10 and 100 nm were obtained, with an electrical charge of approximately −30 mV that directly correlates with stable nanoparticle formulations. Representative graphs of both size and stability are shown in FIGS. 1 and 2.

Example 2

Figure 3:
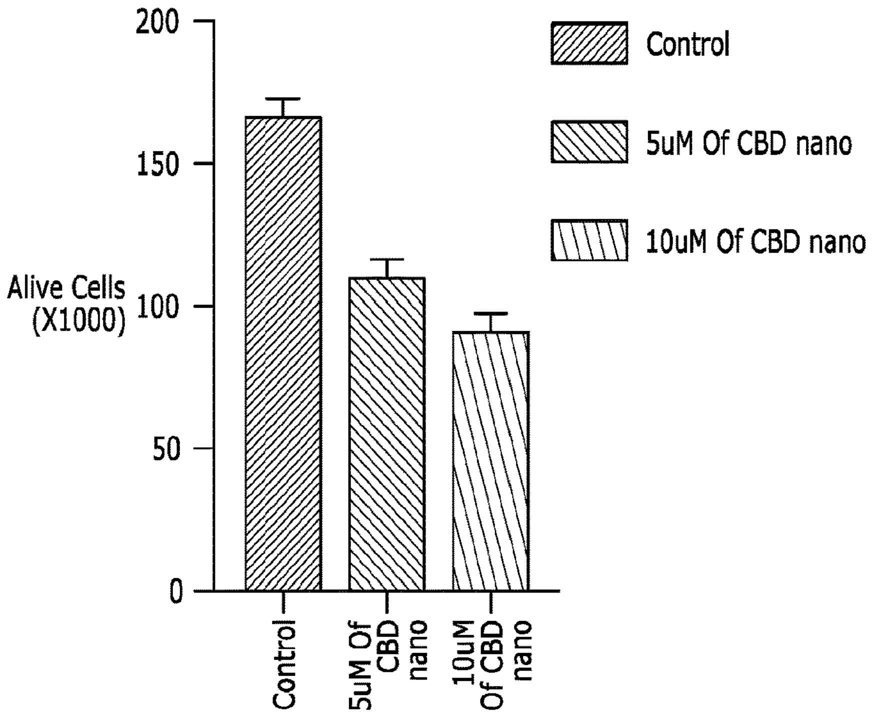
FIG. 3 depicts the dose-dependent ability of nanoparticulate cannabidiol (CBD nano) to kill T-lymphocytes, at 0 μM (control), 5 μM, and 10 OA of nanoparticulate cannabidiol.

An in vitro screening platform for immunomodulation was used to evaluate nanoparticles for efficacy. CTLL-2 (ATCC®TIB-214™) are cytotoxic T lymphocytes that were purchased and cultured according to ATCC protocol. Once confluent, cells were seeded in a 12-well plate at a concentration of 55,000 cells/mL and treated, in triplicates, with the CBD nanoformulations described herein. As indicated in FIG. 3, CBD nanoparticles are shown to dose dependently kill T-lymphocytes.

Figure 4:
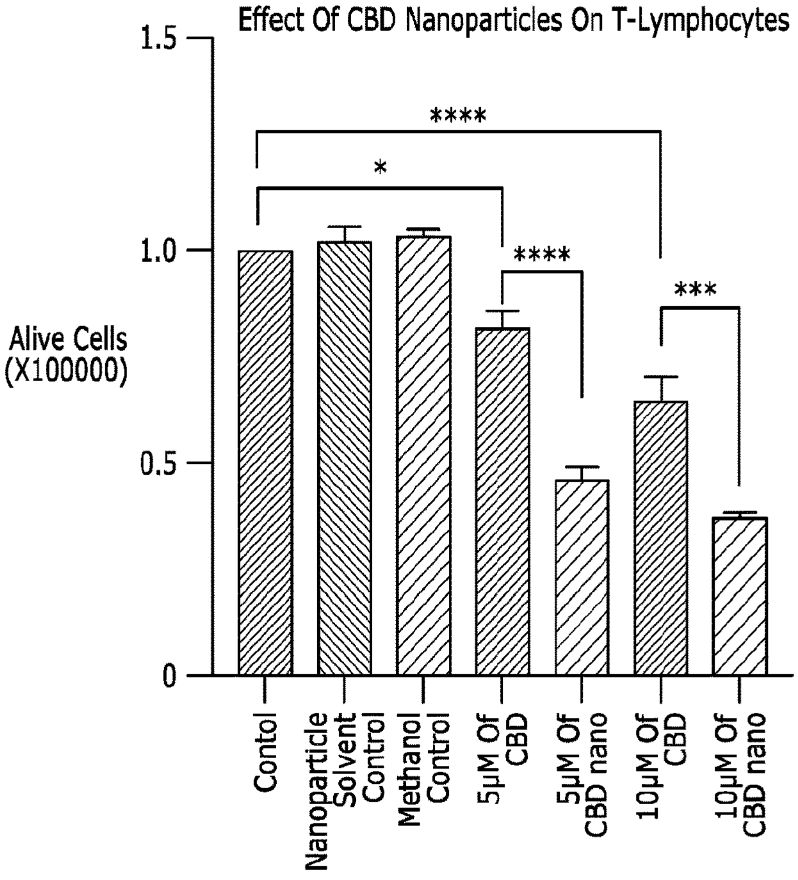
FIG. 4 depicts the dose-dependent ability of cannabidiol (CBD) or nanoparticulate cannabidiol (CBD nano) to kill T-lymphocytes, at 0 μM (control), 5 μM, and 10 OA of cannabidiol.

A similar experiment was carried out using CBD alone (not in nanoformulations). Both CBD and nanoparticulate CBD were shown to be effective in reducing T-lymphocytes compared to controls, as shown in FIG. 4.

CTLL-2 is an effective in vitro platform for evaluating new drugs for the treatment of AA. Using this platform, simvastatin has been shown to be an effective therapeutic agent in reversing AA phenotype in C3H mouse model of AA. The C3H mouse model has also been shown to be an excellent representative animal model for AA in humans. Thus, it is possible to translate this work from the in vitro platform to the human disease. More recently, the inflammatory process has been shown to possibly play a role in other types of AA, including but not limited to male-pattern baldness. Thus, the combination of an immune modulating CBD nanoparticle formulation, which decreases the inflammation that is attributed to inhibition of hair growth, in combination with a hair-growth stimulating agent such as minoxidil, is desirable.

Example 3

In order to investigate options for improving CBD drug delivery in vitro, CBD was also formulated as a carrier-free nanoparticle and evaluated for efficacy. Pure carrier-free CBD nanoparticles were synthesized at a concentration of 127.2 μM and evaluated at 5 and 10 μM concentrations. Increased efficacy in modulation of the cytotoxic T-lymphocytes was observed for CBD nanoparticles in the screening platform compared to CBD alone (in non-nanoparticle formulation) (FIG. 4).

Figure 5A:
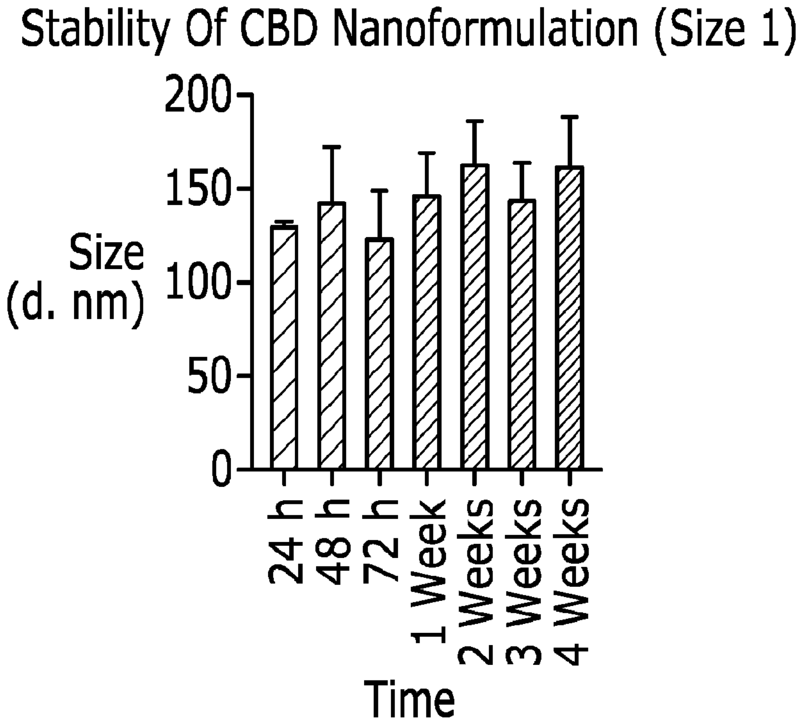
FIGS. 5A, 5B, and 5C depict the stability of CBD nanoformulations. Dynamic light scattering measurements were made over four weeks of monodispersed particles having a hydrodynamic size of about 124.42 nm (5A) and 22.99±2.42 nm (5B), Zeta-potential was used to measure the electrical charge of the nanoparticles over four weeks (5C: ζ-potential-17.5±0.90 mV).
Figure 5B:
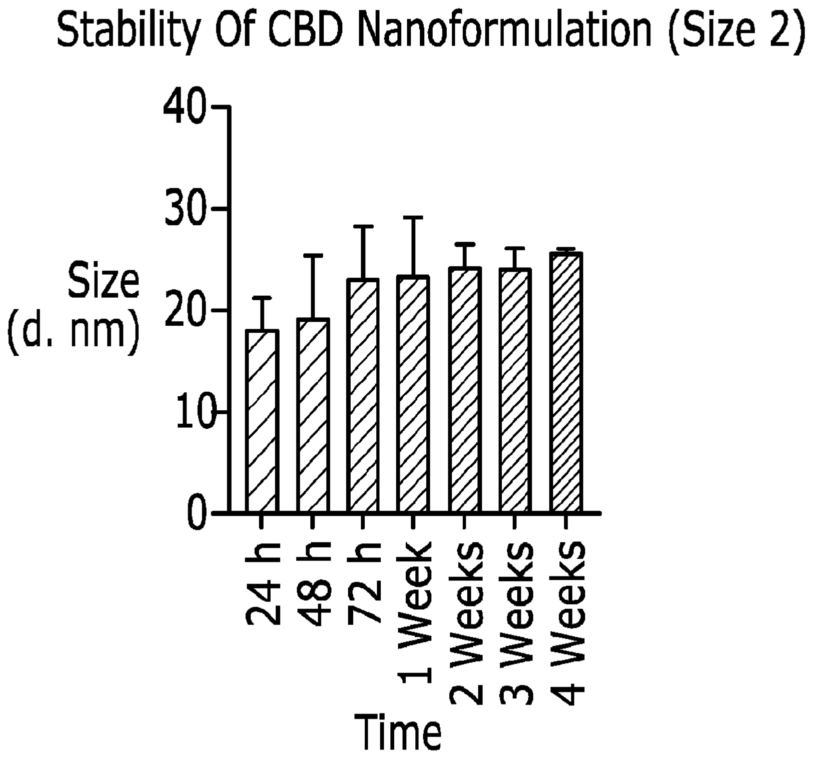
Figure 5C:
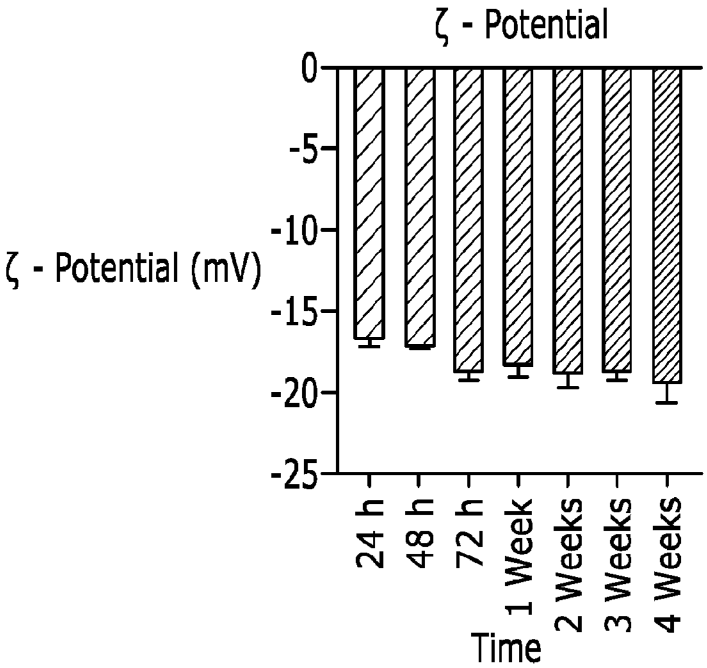

The nanoformulation was characterized using dynamic light scattering to determine the hydrodynamic size of the nanoparticle and ensure reproducibility and homogeneity of nanoformulation. Representative dynamic light scattering graph of hydrodynamic size of nanoparticles indicating monodispersed and reproducible nanoparticles is shown for hydrodynamic sizes 124.42 (FIG. 5A) and 22.99±2.42 nm (FIG. 5B). Zeta-potential was also used to measure the electrical charge of the nanoparticle to directly determine the stability of the nanoparticles in colloid suspension; ζ-potential: −17.5±0.90 mV (FIG. 5C). The stability of CBD nanoformulations was also studied, indicating that the nanoparticles are in fact stable, and no statistically significant change in size or zeta potential was observed after 4 weeks. Data shown is mean±SEM. All experiments were repeated at least three times. No statistically significant difference among means of different time points for size or ζ-potential, indicating a stable CBD nanoformulation regardless of time.

Example 4

In Vivo Experiments

Without wishing to be bound by theory, in the immune model of hair loss, which translates directly to human hair loss, the inflammatory process induced by activated T-cells leads to miniaturization of the hair follicle and eventual alopecia. The recovery process is complex. Again without wishing to be bound by theory, first, the activated T-cells must be deactivated (e.g., with the CBD compositions described herein) and then the hair follicle cells must be stimulated e.g., with the CBD/minoxidil compositions described herein) to generate hair regrowth.

An animal study was carried out to determine the effect of a CBD nanoparticulate formulation comprising minoxidil as described herein on the induction of hair regrowth in alopecia mice after 12 weeks. In order to collect preliminary information on the reversal of Alopecia by CBD/minoxidil, a randomized pilot study on 24 animals was performed.

Eight- to ten-month-old mice with Auto-Immune Alopecia were randomized into four groups (six animals per group), receiving topical treatments daily for 12 weeks. Group 1 (Control group) received 0.1 ml of control solution applied topically over the ventral area daily for 12 weeks. Group 2 (CBD group) received 20 μg of CBD in 0.1 ml of control solution applied topically over the ventral area daily for 12 weeks. Group 3 (minoxidil) received 0.1 ml of 5% minoxidil solution applied topically over the ventral area daily for 12 weeks. Group 4 (CBD/minoxidil) received 20 μg of CBD and 5% minoxidil in 0.1 ml solution applied topically over the ventral area daily for 12 weeks.

Figure 6A:
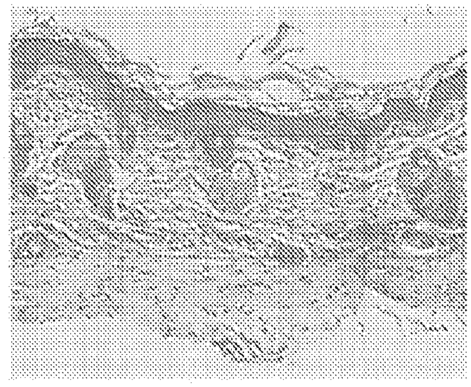
FIGS. 6A, 6B, 6C, and 6D depict representative histopathology of alopecia mouse tissue after 12 weeks. Histopathology shows miniaturization, and no significant effect was observed in control groups of vehicle (6A), CBD alone (6B), and minoxidil alone (6C). Hair follicles the anagen phase were observed in a group treated with CBD and minoxidil (also called "CBD/minoxidil" or "CBD+minoxidil") (6D).
Figure 6B:
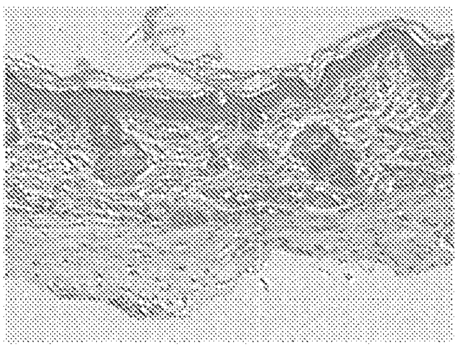
Figure 6C:
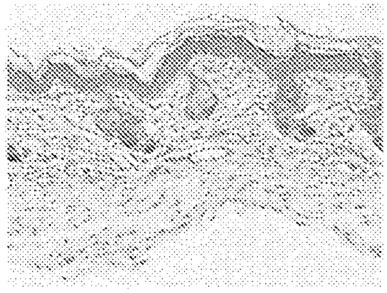
Figure 6D:
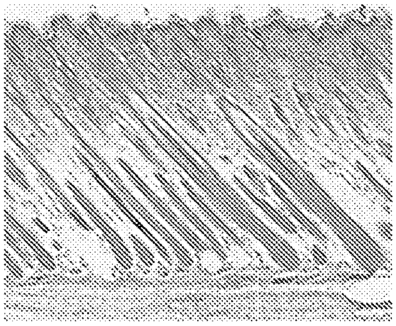

Mice were sacrificed at the end point of a twelve week observation period, and skin biopsies were obtained. Skin biopsies were processed for histopathology. No significant effect was observed in control groups of vehicle (FIG. 6A), CBD alone (FIG. 6B), and minoxidil alone (FIG. 6C). Histopathology showed miniaturization in control groups of vehicle, CBD alone, and minoxidil alone. Hair follicles in the anagen phase were observed in the CBD+minoxidil group (FIG. 6D).

The results are summarized in Table A, below. Reported categories are as follows: 0=no hair growth, 1=0-25% hair regrowth, 2=25-50% hair regrowth, 3=50-75% hair regrowth, 4=75-100% hair regrowth.

TABLE A

| | Number of animals per hair regrowth category | | | | |
|---|---|---|---|---|---|
| | Category 0 | Category 1 | Category 2 | Category 3 | Category 4 |
| Control | 6 | 0 | 0 | 0 | 0 |
| CBD | 6 | 0 | 0 | 0 | 0 |
| Minoxidil | 6 | 0 | 0 | 0 | 0 |
| CBD/Minoxidil | 0 | 0 | 1 | 3 | 2 |

In the above results, none of the control (vehicle), CBD alone, or minoxidil alone mice showed significant hair regrowth. In contrast, a CBD/minoxidil combination as disclosed herein exhibited a synergistic, strong hair regrowth effect in all treated mice.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference.

REFERENCES

1. Gilhar et al., N Engl J Med. 2012; 366(16):1515-25.
2. Korta et al., J Am Acad Dermatol. 2018; 78(4):832-4.

3. Darwin et al., Int J Trichology. 2018; 10(2):51-60.
4. Anzai et al., Int Immunol. 2019; 31(7):439-47.
5. Foundation NAA. What you need to know about alopecia areata National Alopecia Areata Foundation 2019.
6. Pratt et al., Nat Rev Dis Primers. 2017; 3:17011.
7. Speiser et al., J Cutan Pathol. 2019; 46(9):653-8.
8. Hamed et al., PLoS One. 2019; 14(7):e0210308.
9. Kalekar et al., Int Immunol. 2019; 31(7):457-63.
10. Han et al., J Dermatol. 2015; 42(10):981-8.
11. Dermatology AAo. Alopecia areata: American Academy of Dermatology; 2018.
12. Strazzulla et al., J Am Acad Dermatol. 2018; 78(1):15-24.
13. Shapiro et al., J Investig Dermatol Symp Proc. 2013; 16(1):S42-4.
14. Cranwell et al., Australas J Dermatol. 2019; 60(2):163-70.
15. Pisanti et al., Pharmacol Ther. 2017; 175:133-50.
16. Kaplan et al., Biochem Pharmacol. 2008; 76(6):726-37.
17. Katchan et al., Autoimmun Rev. 2016; 15(6):513-28.
18. Kozela et al., Br J Pharmacol. 2011; 163(7):1507-19.
19. Mecha et al., Neurobiol Dis. 2013; 59:141-50.
20. Malfait et al., Proc Natl Acad Sci USA. 2000; 97(17):9561-6.
21. Mechoulam et al., Chem Biodivers. 2007; 4(8):1678-92.
22. Weiss et al., Autoimmunity. 2006; 39(2):143-51.
23. Dhital et al., Cell Immunol. 2017; 312:25-34.
24. Cunha et al., Pharmacology. 1980; 21(3):175-85.
25. Hammell et al., Eur J Pain. 2016; 20(6):936-48.
26. Mechoulam et al., J Clin Pharmacol. 2002; 42(S1):11S-9S.
27. Millar et al., Front Pharmacol. 2018; 9:1365.
28. Bartner et al., Can J Vet Res. 2018; 82(3):178-83.
29. Lodzki et al., J Control Release. 2003; 93(3):377-87.
30. Molecules. 2018; 23(10).
31. Barry et al., Eur J Pharm Sci. 2001; 14(2):101-14.
32. Peyravian et al., Prog Neurobiol. 2019:101679.

We claim:

1. A topical composition consisting of:

(a) nanoparticulate cannabidiol consisting of greater than 98% by weight cannabidiol and having an average particle size of about 5 nm to about 200 nm; and (b) a pharmaceutically acceptable carrier, wherein the nanoparticulate cannabidiol is capable of penetrating into the skin, wherein the nanoparticulate cannabidiol is substantially free of lipid or polymeric nanocarriers, and wherein the nanoparticulate cannabidiol is present in the topical composition at a concentration of about 5 μM to about 10 μM.

2. The topical composition of claim 1, wherein the nanoparticulate cannabidiol is monodisperse.

3. The topical composition of claim 1, wherein the pharmaceutically acceptable carrier is a nanosphere, nanoassembly, nanoaerosol, or nanomicelle.

4. The topical composition of claim 1, wherein the nanoparticulate cannabidiol is capable of penetrating into the epidermis or dermis.

5. A topical composition consisting of:

(a) nanoparticulate cannabidiol consisting of greater than 98% by weight cannabidiol;

(b) minoxidil; and (c) a pharmaceutically acceptable carrier consisting of ethanol, propylene glycol, water and optionally one or more of solvent, antisolvent and adjuvant, wherein the cannabidiol is present at a concentration of about 200 g/ml and the minoxidil is present at a concentration of about 5% by weight.

6. The topical composition of claim 5, wherein the cannabidiol is capable of penetrating into the epidermis or dermis.

7. A method of treating alopecia areata in a subject, the method comprising administering to the subject a therapeutically effective amount of the topical composition of claim 1.

8. The method of claim 7, further comprising treating or preventing hair loss.

9. The method of claim 7, further comprising administering to the subject minoxidil.

10. The topical composition of claim 1, wherein the nanoparticulate cannabidiol has an average particle size of about 10 nm to about 100 nm.

11. The topical composition of claim 1, wherein the nanoparticulate cannabidiol has an average particle size of about 20 nm.

12. The topical composition of claim 1, wherein the nanoparticulate cannabidiol has an average particle size of about 120 nm.

13. The topical composition of claim 1, wherein the nanoparticulate cannabidiol is present in the topical composition at a concentration of about 5 μM.

14. The topical composition of claim 1, wherein the nanoparticulate cannabidiol is present in the topical composition at a concentration of about 10 μM.

15. The method of claim 7, wherein the pharmaceutically acceptable carrier is a nanomicelle.

16. The method of claim 7, wherein the pharmaceutically acceptable carrier consists of ethanol, propylene glycol, water and optionally one or more of solvent, antisolvent and adjuvant.

17. A method of treating alopecia areata in a subject, the method comprising administering to the subject a therapeutically effective amount of the topical composition of claim 15.

18. The method of claim 17, further comprising treating or preventing hair loss.

* * * * *